United States Patent
Gregory

(10) Patent No.: US 10,736,536 B2
(45) Date of Patent: Aug. 11, 2020

(54) TECHNIQUES FOR PREDICTING RECURRENCE OF CANCEROUS CELLS USING IMPEDANCE DETECTION

(71) Applicant: NovaScan, Inc., Milwaukee, WI (US)

(72) Inventor: William David Gregory, Shorewood, WI (US)

(73) Assignee: NOVASCAN, INC., Milwaukee, WI (US)

(*) Notice: Subject to any disclaimer, the term of this patent is extended or adjusted under 35 U.S.C. 154(b) by 0 days.

(21) Appl. No.: 16/288,001

(22) Filed: Feb. 27, 2019

(65) Prior Publication Data

US 2019/0216358 A1 Jul. 18, 2019

Related U.S. Application Data

(63) Continuation-in-part of application No. 15/870,804, filed on Jan. 12, 2018.

(60) Provisional application No. 62/636,798, filed on Feb. 28, 2018.

(51) Int. Cl.
*A61B 5/053* (2006.01)
*G01N 33/483* (2006.01)
*A61B 5/00* (2006.01)
*A61B 18/14* (2006.01)
*A61B 18/00* (2006.01)

(52) U.S. Cl.
CPC ........... *A61B 5/0536* (2013.01); *A61B 5/742* (2013.01); *A61B 5/7475* (2013.01); *G01N 33/483* (2013.01); *A61B 2018/00732* (2013.01); *A61B 2018/00875* (2013.01); *A61B 2018/147* (2013.01)

(58) Field of Classification Search
CPC ........... A61B 5/053; A61B 5/0536; A61B 2018/0016; G01N 27/026; G01N 27/04; G01N 33/4836; G01N 33/4833
See application file for complete search history.

(56) References Cited

U.S. PATENT DOCUMENTS

| 4,472,506 A | 9/1984 | Liburdy |
| 8,467,865 B2 | 6/2013 | Gregory et al. |
| 2005/0177062 A1 | 8/2005 | Skrabal et al. |
| 2009/0253193 A1* | 10/2009 | Gregory ............ G01N 33/4836 435/287.1 |

(Continued)

OTHER PUBLICATIONS

Gregory, W. D. et al. "The Cole relaxation frequency as a parameter to identify cancer in breast tissue." Medical Physics (2012) 39 4167-4174. (Year: 2012).*

(Continued)

*Primary Examiner* — Christopher Adam Hixson
(74) *Attorney, Agent, or Firm* — Artegis Law Group, LLP

(57) ABSTRACT

One embodiment of the present application sets forth a method for predicting recurrence of cancerous cells in a patient that includes measuring, by a first subset of electrodes included in an electrode array operating at a first frequency, a first impedance of a first section of a first sample of tissue excised from the patient, computing a first Cole relaxation frequency for the first section of the first sample based on the first impedance, and generating a first prediction relating to cancerous cells in the patient based at least in part on the first Cole relaxation frequency.

20 Claims, 7 Drawing Sheets

(56) References Cited

U.S. PATENT DOCUMENTS

2010/0191141 A1 7/2010 Aberg
2018/0206755 A1 7/2018 Gregory et al.

OTHER PUBLICATIONS

Walijee, Jennifer F. et al. "Predictors of re-excision among women undergoing breast-conserving surgery for cancer." Annals of Surgical Oncology (2008) 15 1297-1303. (Year: 2008).*

International Search Report for application No. PCT/US2019/020089 dated May 10, 2019.

Mikkelson et al., "The Cole Relaxation Frequency as a Parameter to identify Cancer in Breast Tissue", American Association of Physicists in Medicine, URL : http://www.novascaninc.com/pdf/Poster_Printout_ASBrS_Annual_Meeting.pdf, vol. 39, No. 7, Jun. 18, 2012, 14 pages.

* cited by examiner

Combined BCC + SCC Results — 510

| N = 206 | Pathology: Neg | Pathology: Pos | |
|---|---|---|---|
| Device: Neg | 124 | 2 | 126 |
| Device: Pos | 2 | 78 | 80 |
| | 126 | 80 | |

Accuracy = 98.06%  
Misclassification rate = 1.94%  
Sensitivity / TPR = 97.50%  
FPR = 1.59%  
Specificity = 98.41%

SCC Results — 520

| N = 29 | Pathology: Neg | Pathology: Pos | |
|---|---|---|---|
| Device: Neg | 22 | 0 | 22 |
| Device: Pos | 0 | 7 | 7 |
| | 22 | 7 | |

Accuracy = 100.00%  
Misclassification rate = 0.00%  
Sensitivity / TPR = 100.00%  
FPR = 0.00%  
Specificity = 100.00%

BCC Results — 530

| N = 177 | Pathology: Neg | Pathology: Pos | |
|---|---|---|---|
| Device: Neg | 102 | 2 | 104 |
| Device: Pos | 2 | 71 | 73 |
| | 104 | 73 | |

Accuracy = 97.74%  
Misclassification rate = 2.26%  
Sensitivity / TPR = 97.30%  
FPR = 1.92%  
Specificity = 98.08%

(TP+TN)/total  
(FP+FN)/total  
TP/actual yes  
FP/actual no  
TN/actual no

FIG. 5

TECHNIQUES FOR PREDICTING RECURRENCE OF CANCEROUS CELLS USING IMPEDANCE DETECTION

CROSS-REFERENCE TO RELATED APPLICATIONS

This application is a continuation-in-part of the co-pending U.S. patent application titled, "TECHNIQUES FOR DETECTING CANCEROUS CELLS IN EXCISED TISSUE SAMPLES USING IMPEDANCE DETECTION," filed on Jan. 12, 2018 and having Ser. No. 15/870,804. This application also claims priority benefit to the U.S. Provisional Patent Application titled, "TECHNIQUES FOR PREDICTING RECURRENCE OF CANCEROUS CELLS USING IMPEDANCE DETECTION," filed on Feb. 28, 2018 and having Ser. No. 62/636,798. The subject matter of these related applications is hereby incorporated herein by reference.

BACKGROUND OF THE INVENTION

Field of the Invention

Embodiments of the present invention relate generally to medical diagnostic technology, and, more specifically, to techniques for predicting recurrence of cancerous cells using impedance detection.

Description of the Related Art

In various medical procedures, various tissue cells is excised from a patient and analyzed in order for an analyst to make various diagnoses for a patient. For example, skin tissue samples can be excised and analyzed during surgery. One such example is Mohs micrographic surgery (MMS), which is a treatment for skin cancer that is used when removing basal cell carcinomas (BCCs) and squamous cell carcinomas (SCCs). During MMS, a surgeon removes a layer of skin from a target area of a patient that is suspected to include some cancer cells. Immediately after removing the excised layer, frozen sections are prepared and the surgeon examines slides under a microscope to identify the presence of cancer cells. Throughout the procedure, the surgeon successively removes skin layers from the patient and examines the removed skin layers until one or more excised skin layers are satisfactorily cleared of diseased tissue. MMS advantageously enables a surgeon to remove a minimal amount of tissue from the patient and preserve a maximal amount of healthy cells around the target excision.

One of the drawbacks of MMS is that excising, examining, and assessing the different layers of tissue suspected to contain cancer cells is quite time-consuming for surgeons. In particular, as alluded to above, for each excised layer of tissue, the surgeon must manually prepare frozen sections and then examine frozen sections under a microscope and assess whether the sample contains any cancer cells. Due to the time-consuming nature of MMS, this particular procedure is considered to be an expensive form of cancer treatment.

As the foregoing illustrates, what is needed in the art are more effective techniques for analyzing and assessing excised tissue layers during Mohs micrographic surgery.

SUMMARY OF THE INVENTION

One embodiment of the present application sets forth a method for predicting recurrence of cancerous cells in a patient that includes measuring, by a first subset of electrodes included in an electrode array operating at a first frequency, a first impedance of a first section of a first sample of tissue excised from the patient, computing a first Cole relaxation frequency for the first section of the first sample based on the first impedance, and generating a first prediction relating to cancerous cells in the patient based at least in part on the first Cole relaxation frequency.

A major advantage of the disclosed tissue analysis system is that the system quickly and accurately detects the presence and location of cancer cells within a tissue excised from a patient, without involving the surgeon. Further, the tissue analysis system reliably analyzes excised tissue to predict the probability that cancer recurs in a patient and whether the recurrence of the cancer will eventually lead to metastasis. Because the disclosed system is able to automatically analyze and assess successively excised tissue layers in an MMS procedure before the preparation of frozen sections, the time required to perform MMS is substantially reduced, thereby making MMS a more cost-effective form of cancer treatment. Further, the disclosed system enables a user to reliably determine the probability of cancer recurrence, which may lead to specific treatments related to a cancer recurrence and metastasis.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 5 illustrates tables showing the accuracies of cancer detection in a sample group of patients based on various computed Cole relaxation frequencies, according to various embodiments of the present invention;

DETAILED DESCRIPTION

Figure 1:
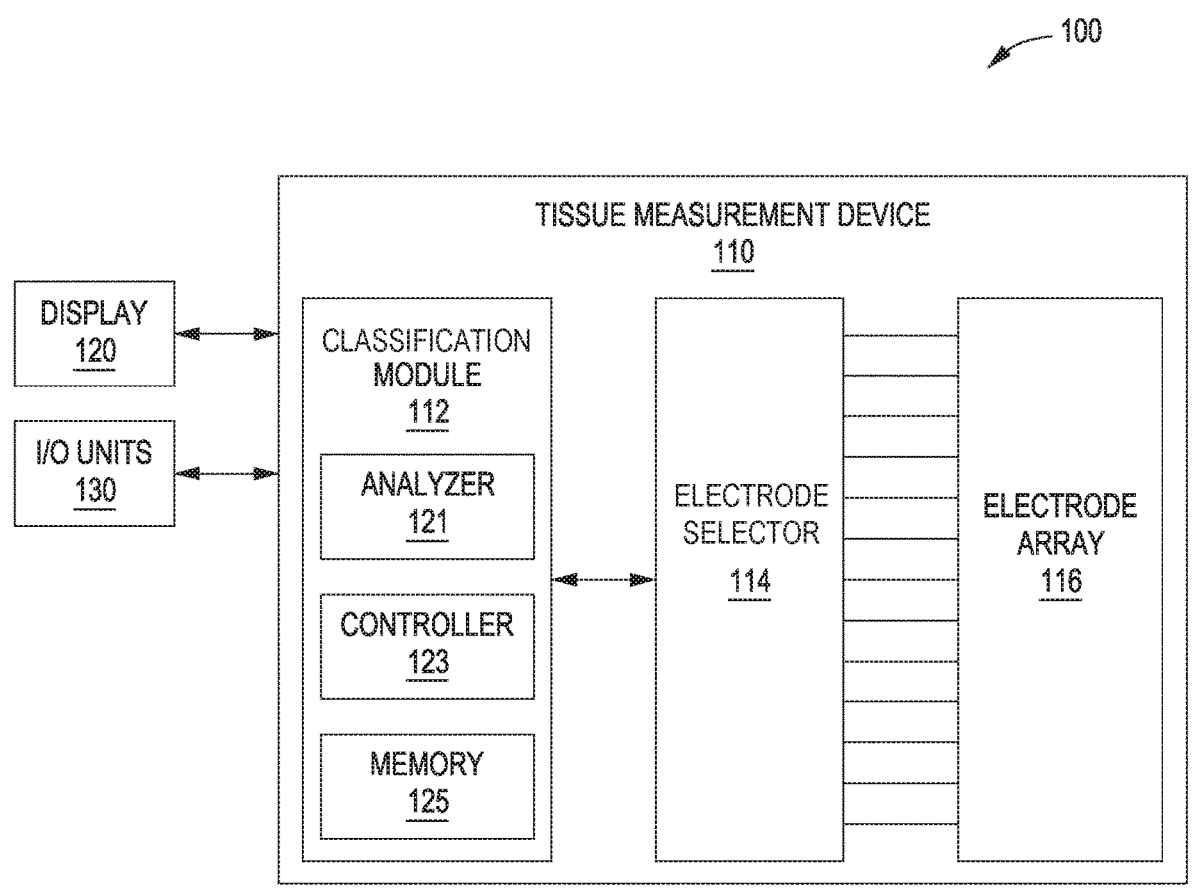
FIG. 1 illustrates a tissue measuring system configured to implement one or more aspects of the present invention.

In the following description, numerous specific details are set forth to provide a more thorough understanding of the present invention. However, it will be apparent to one of skilled in the art that the present invention may be practiced without one or more of these specific details.

As discussed above, conventional techniques for Mohs micrographic surgery (MMS) require a surgeon to excise and manually prepare frozen sections for microscopic evaluation of excised skin tissue to determine whether the excised tissue contains any cancer cells. Such a technique is time-consuming and expensive, as the lengthy process requires the surgeon or third party to perform assessments for several frozen sections of each of the excised layers during the surgery.

To address this problem, embodiments of the invention include a tissue measuring system that sends electrical currents to specified sections of an excised tissue sample via an electrode array. A diagnosis module connected to the electrode array receives electrical measurements and computes electrical properties, including impedances, Cole relaxation frequencies, and/or an electronic transformation age based on the electrical measurements. The diagnosis module compares one or more computed Cole relaxation frequencies to a cancer-detection threshold to determine whether cancerous cells are present in the corresponding sections of the excised tissue sample. In some embodiments, the diagnosis module may determine the locations of the detected cancerous cells within the excised tissue sample.

The diagnosis module also compares the electronic transformation age to a recurrence threshold to determine whether cancer cells, once excised, would recur in a subject. The electronic transformation age (ETA) reflects the characteristics of a tissue cell exhibiting increasing values for a relaxation frequency as the cell gradually transforms from benign to cancerous over a long period of time. As the electronic transformation age increases, the likelihood for cancer recurrence and/or metastasis increases. In various embodiments, the diagnosis module compares the computed electronic transformation age to a metastasis threshold to determine whether cancerous cells, once excised, would recur and metastasize in a subject. The diagnosis module generates a prediction for cancer recurrence and/or metastasis based on comparing the electronic transformation age to the respective thresholds.

Though the description discusses skin tissue samples excised during Mohs micrographic surgery, the disclosed techniques can be executed for other types of excised tissues cells. Further, the disclosed techniques can be executed independently from MMS procedures.

Throughout this disclosure, the following terms describe the operation of the tissue measuring system.

Impedance is a response of a given system, composed of conducting material and/or dielectric material, to the excitation by an external alternating electric field. Impedance of a given system is a ratio of voltage to current and includes two components: resistance and reactance. For cells, the resistive component typically drops as a frequency of an input signal increases. The reactive component reaches a minimum at a characteristic frequency, which generally occurs at the half-way point of the frequency range.

Relaxation frequency is the rate at which cells dissipate a deposited electrical charge during excitation. Generally, a measuring device injects an electrical charge and measures the rate at which the electrical charge dissipates. In various embodiments, a measuring device may use an equivalent circuit model for current-conduction paths in the cell (or groups of cells) that are intact tissue, or cells in suspension. The Cole relaxation frequency is the characteristic frequency of the cell, as obtained by fitting the measured data, relating to the intact live tissue, to the Cole equation.

Electrode polarization (EP) is a phenomenon that occurs where an isolating barrier forms at the interface between the tissue and the electrode. EP occurs due to the mismatch of the tissue conducting with ions and the electrode conducting with electrons, where the ions cannot move into the electrode. In various embodiments, excess charges due to EP can contribute to the voltage measured by the measuring device. The excess charge is proportional to a value of Q/A, where Q is the EP charge and A is the surface area of the electrode. In various embodiments, the measuring device mitigates the excess charge using one or more techniques, such as specific measuring techniques, using specific electrodes, and/or coatings on the electrodes.

In various embodiments, an electrochemical coating on a given electrode may reduce EP during measurement. For example, a silver chloride coating on silver electrodes (Silver-Silver Chloride) is shown to reduce EP due to the presence of chlorine ions on the electrodes. Additionally or alternatively, a blackened platinum (BPt) electrode may be included in the measuring device. For example, platinum can be more robust than silver for electrodes and substantially inert. In various embodiments, smooth platinum may be rapidly electrodeposited with more platinum, creating a rough surface at an atomic level, increasing the surface area (up to 10,000 times) over smooth platinum. A measuring device using the coating and/or platinum electrodes reduces the effect of EP by increasing the surface area, thus reducing the $Q/A$ ratio.

In various embodiments, the measuring device uses a four-lead impedance measurement to reduce the impact of EP during measurements. For example, the measuring device can use a four-lead measurement configuration, where the voltage is measured by two leads that have little current flowing, such through use of high-impedance input amplifiers. In such instances, the other two lead electrodes respectively inject and extract current. The current is measured in a current loop, which causes the EP to be measured and accounted for when the measuring device determines the ratio of voltage to current. Additionally or alternatively, the measuring device may use two-lead impedance measurements. In such instances, the measuring device measures the current and the voltage with the same electrode. The measuring device is capable of making accurate measurements with two leads when the electrodes are treated to mitigate EP effects.

FIG. 1 illustrates a tissue measuring system configured to implement one or more aspects of the present invention. Tissue analysis system 100 includes tissue measurement device 110, display 120, and input/output (I/O) units 130. Tissue measurement device 110 includes classification module 112, electrode selector 114, and an electrode array 116. Classification module 112 includes analyzer 121, controller 123, and memory 125. In some embodiments, tissue measurement device 110 may include classification module 112, electrode selector 114, and electrode array 116 as separate physical components. In alternative embodiments, classification module 112, electrode selector 114, and/or electrode array 116 may share a common housing. Additionally or alternatively, tissue measurement device 110 may communicate wirelessly with display 120 and/or I/O units 130.

Tissue measurement device 110 automatically measures impedances of a section of an excised tissue sample. Classification module 112 causes electrode selector 114 to select different measuring subsets of electrode array 116. A selected measuring subset of electrode array 116 measures electrical properties of a given section of an excised tissue sample. In some embodiments, when performing measurements on a given section of the excised tissue sample via a selected measuring subset, classification module 112 may perform a sweep of measurements within a specified operating frequency range. For example, a measuring subset of electrode array 116 could initially inject a current at an initial operating frequency between 1 kHz and 25 MHz, and then measure and record the electrical properties of the corresponding section of the excised tissue sample. Tissue measurement device 110 could then sweep through range of operating frequencies using the selected measuring subset. For example, tissue measurement device 110 could increase the operating frequency of the injecting current at steps of 1 kHz, and record the electrical properties of the corresponding section of the excised tissue sample.

Tissue measurement device 110 computes impedances for the electrical properties and subsequently computes a relaxation frequency from the computed impedances. The relaxation frequency for a section of the excised tissue sample reflects the rate at which a cell membrane discharges a stored electrical charge. In various embodiments, tissue measurement device may compute one or more specific frequencies, such as the Cole relaxation frequency, when the collected data fits the Cole equation. Though tissue measurement device 110 computes a Cole relaxation frequency, any technically-feasible relaxation frequency that can be computed in by tissue measurement device 110 is within the scope of the various embodiments.

In some embodiments, tissue measurement device 110 may compute the relaxation frequency for a given section of the excised tissue sample as an average of electrical discharge rates for a plurality of cells included in the given section of the excised tissue sample. In some embodiments, tissue measurement device 110 may determine the presence and/or location of cancerous cells based on computing relaxation frequencies for one or more sections of the excised tissue sample. Additionally or alternatively, tissue measurement device 110 may output measurement data to display 120 and/or I/O units 130.

Electrode array 116 includes multiple electrodes that are electrically isolated from each other by intervening channels. In some embodiments, electrode array 116 is planar, allowing an excised tissue sample to be placed directly on one or more electrodes of electrode array 116. Additionally or alternatively, one or more of the electrodes included in electrode array 116 may be non-invasive and may have a surface configured to reduce electrical polarization between individual electrodes of electrode array 116 and the excised tissue sample. For example, one or more of the electrodes in electrode array 116 could have a blackened platinum (BPt) surface that physically contacts a portion of the excised tissue sample, reducing the electrical polarization between the electrode array 116 and the excised tissue sample.

Electrode selector 114 connects electrical signals between electrode array 116 and classification module 112. In various embodiments, electrode selector 114 includes components of measurement circuits, including a voltmeter and/or an ammeter. In such instances, electrode selector 114 may connect a measuring subset of electrodes from electrode array 116 to the voltmeter and/or the ammeter, respectively, to measure the voltage and/or current of the section of the excised tissue sample.

Electrode selector 114 includes hardware and/or software to connect a subset of electrodes to form a measuring circuit. For example, electrode selector 114 could include an array of individual switches, such as micro-relay circuits, that each connect to a separate electrode in electrode array 116. In such instances, the individual switches could be controlled by controller 123 in classification module 112 to connect the corresponding electrodes to either a current-sensing circuit and/or a voltage-sensing circuit. Additionally or alternatively, electrode selector 114 may include one or more mechanical switches to connect one or more electrodes included in electrode array 116 while isolating the remaining electrodes. Each of the current-sensing circuit and the voltage-sensing circuit could be components of a single measurement circuit. In some embodiments, electrode selector 114 may keep one or more micro-relays included in the micro-relay circuits open, where the connected electrode remains floating and provides high impedance when a current is injected.

Classification module 112 connects to electrode array 116 via electrode selector 114. Classification module 112 includes a processing unit. The processing unit can be a single central processing unit (CPU), or combination of processing units. The processing unit can be any technically-feasible hardware unit capable of processing data and/or executing software code. In some embodiments, the processing unit of classification module 112 may receive instructions from a user and/or from memory 125 and may execute instructions. Additionally or alternatively, the processing unit may implement one or more techniques executed by analyzer 121 and/or controller 123.

For example, classification module 112 could receive instructions from a user via I/O units 130 to store data and/or to perform specific electrical measurements via electrode array 116. Classification module 112 could then use controller 123 to execute a program stored in memory 125 to conduct one or more electrical measurements on the excised tissue sample using one or more measuring subsets of electrode array 116. In some embodiments, classification module 112 may store the measured electrical properties, as determined by the measurement circuit. The measured electrical properties can include, for example, the measured voltage and the measured current for an input signal at a specific operating frequency. Additionally or alternatively, controller 123 could execute the program to compare the one or more electrical measurements to one or more pre-defined thresholds and make one or more cancer recurrence predictions based on each of the comparisons.

Analyzer 121 of classification module 112 computes, based on the measured electrical properties received from electrode array 116, real and/or imaginary impedances for a section of the excised tissue sample. In some embodiments, classification module 112 stores the computed impedances in memory 125. Based on the computed impedances, analyzer 121 computes one or more Cole relaxation frequencies for sections of the excised tissue samples. In various embodiments, analyzer 121 may generate a cancer recurrence prediction based at least on the one or more computed Cole relaxation frequencies.

Analyzer 121 computes a Cole relaxation frequency for a section of an excised tissue sample based on impedances corresponding to the operating frequency. The Cole relaxation frequency for a section of the excised tissue sample reflects the rate at which a cell membrane discharges a stored electrical charge. In some embodiments, analyzer 121 determines whether the section of the excised tissue sample includes cancerous cells. Due to the contrasting electrical properties of malignant cells and non-malignant cells, malignant cells have a Cole relaxation frequency that is over one thousand times larger than the Cole relaxation frequency of a non-malignant cell. Analyzer 121 compares the computed Cole relaxation frequency to a pre-determined cancer-detection threshold to determine whether the section of the excised tissue sample contains cancerous cells.

In various embodiments, analyzer 121 may determine a probability of the presence of malignant cancer cells based on one or more frequency ranges above the cancer-detection threshold. In such instances, each frequency range may indicate that the cancerous cells are more dangerous and may indicate a need for more aggressive treatment. For example, an initial cancer-detection threshold for breast cancer cells could be 100 kHz and a cancer-recurrence threshold of 300 kHz, and a metastasis threshold of 600 kHz. A Cole relaxation frequency occurring within a first critical range of 100 kHz to 300 kHz could indicate that cancerous cells relating to breast cancer are present, but not likely to recur. A Cole relaxation frequency within a second critical range of 300 kHz to 600 kHz could indicate that the breast cancer may recur after treatment, but not metastasize. A Cole relaxation frequency occurring within a third critical range above 600 kHz could indicate a high likelihood of metastasis after treatment. The cancer-detection threshold and the number and thresholds for each of the critical ranges can vary for each type of cancer.

In various embodiments, analyzer 121 computes an electronic transformation age based on the Cole relaxation frequency. The electronic transformation age (ETA) is a dimensionless ratio directly proportional to the Cole relaxation frequency. For example, analyzer 121 can generate an electronic transformation age by dividing a Cole relaxation frequency by 100 kHz. Analyzer 121 can then compare the electronic transformation age to one or more cancer recurrence thresholds. After comparing the electronic transformation age to the one or more cancer recurrence thresholds, analyzer 121 could then generate a predictive parameter that predicts whether cancer will recur in a patient after surgery and therapy.

As a non-limiting example, classification module 112 could store a lookup table in memory 125 based on the multiple cancer recurrence thresholds. The cancer recurrence thresholds could include a cancer presence threshold of 1, a cancer recurrence threshold of 3, and a metastasis threshold of 6. Based on these thresholds, analyzer 121 could retrieve a cancer recurrence prediction based on the range of the electronic transformation age. Table 1 lists an exemplary lookup table with ETA ranges and corresponding cancer recurrence predictions.

TABLE 1

Cancer Recurrence Prediction Table for Ranges of Cole Relaxation Frequencies

| Cole Relaxation Frequency | ETA | Cancer Recurrence Prediction |
| --- | --- | --- |
| <100 kHz | <1 | No Cancer |
| 100 kHz-300 kHz | 1-3 | Cancer, No Recurrence |
| 300 kHz-600 kHz | 3-6 | Cancer Recurrence without Metastasis |
| >600 kHz | >6 | Cancer Recurrence with Metastasis |

In some embodiments, analyzer 121 generates an impedance spectrum for a set of computed impedances, which indicates the resistive and reactive components of the impedances as a function of the operating frequency used during measurement. In such instances, analyzer 121 can compute the Cole relaxation frequency for the set of impedances by performing a regression analysis to find a best fit to pre-defined impedance spectrums stored in memory 125. Analyzer 121 can determine the Cole relaxation frequency from the impedance spectrum by determining the frequency corresponding to the peak impedance of the negative of the reactive component of the impedance spectrum.

Controller 123 of classification module 112 causes electrode selector 114 to select and connect different measuring subsets of electrode array 116. Each selected measuring subset measures electrical properties of a particular section of an excised tissue sample. Controller 123 also sets the operating frequency and amplitude of the injection current when initiating a measurement using the measuring subset of electrode array 116. In some embodiments, controller 123 may load instructions stored in memory 125 and/or execute a measurement program using one or more measuring subsets of electrode array 116.

For example, controller 123 could generate and transmit one or more control signals to electrode selector 114 to open and/or close switches or otherwise connect to different measuring subsets of electrode array 116. In another example, controller 123 could transmit control signals to electrode selector 114 to connect one or more electrodes included in a measuring subset while disconnecting all other electrodes included in electrode array 116. In various embodiments, controller 123 may change to a different measuring subset by transmitting a control signal to electrode selector 114, where electrode selector 114 electrically connects electrodes of the measuring subset to the measuring circuit, while disconnecting all remaining electrodes in electrode array 116.

Memory 125 is configured to store data and/or software applications. Memory 125 can include a random access memory (RAM) module, hard disk, flash memory unit, or any other type of memory unit or combination thereof. Classification module 112 and I/O units 130 are configured to read data from memory 125. Classification module 112 and I/O units 130 are also configured to write data to memory 125.

Display 120 displays data transmitted from tissue measurement device 110. In some embodiments, display 120 displays one or more of the computed Cole relaxation frequencies, the location(s) of cancerous cell regions, the probability of cancer in the excised tissue sample, and/or a prediction relating to cancer recurrence. In some embodiments, display 120 may refresh the data received from tissue measurement device 110 while tissue measurement device 110 performs measurements on the excised tissue sample. Additionally or alternatively, display 120 may display and image of the excised tissue sample with indications of the locations of probable cancerous cells.

I/O units 130 receive output signals from tissue measurement device 110 and transmit input signals from a user to tissue measurement device 110. In some embodiments, I/O units 130 transmit program input signals to classification module 112, where classification module 112 stores the program in memory 125. In some embodiments, I/O units 130 may include devices capable of receiving one or more inputs, including a keyboard, mouse, input tablet, camera, and/or three-dimensional (3D) scanner. In some embodiments, I/O units 130 may also include devices capable of providing one or more outputs, such as a speaker or printer. In various embodiments, I/O units 130 may include devices capable of both receiving inputs and providing outputs, such as a touchscreen and a universal serial bus (USB) port.

Figure 2:
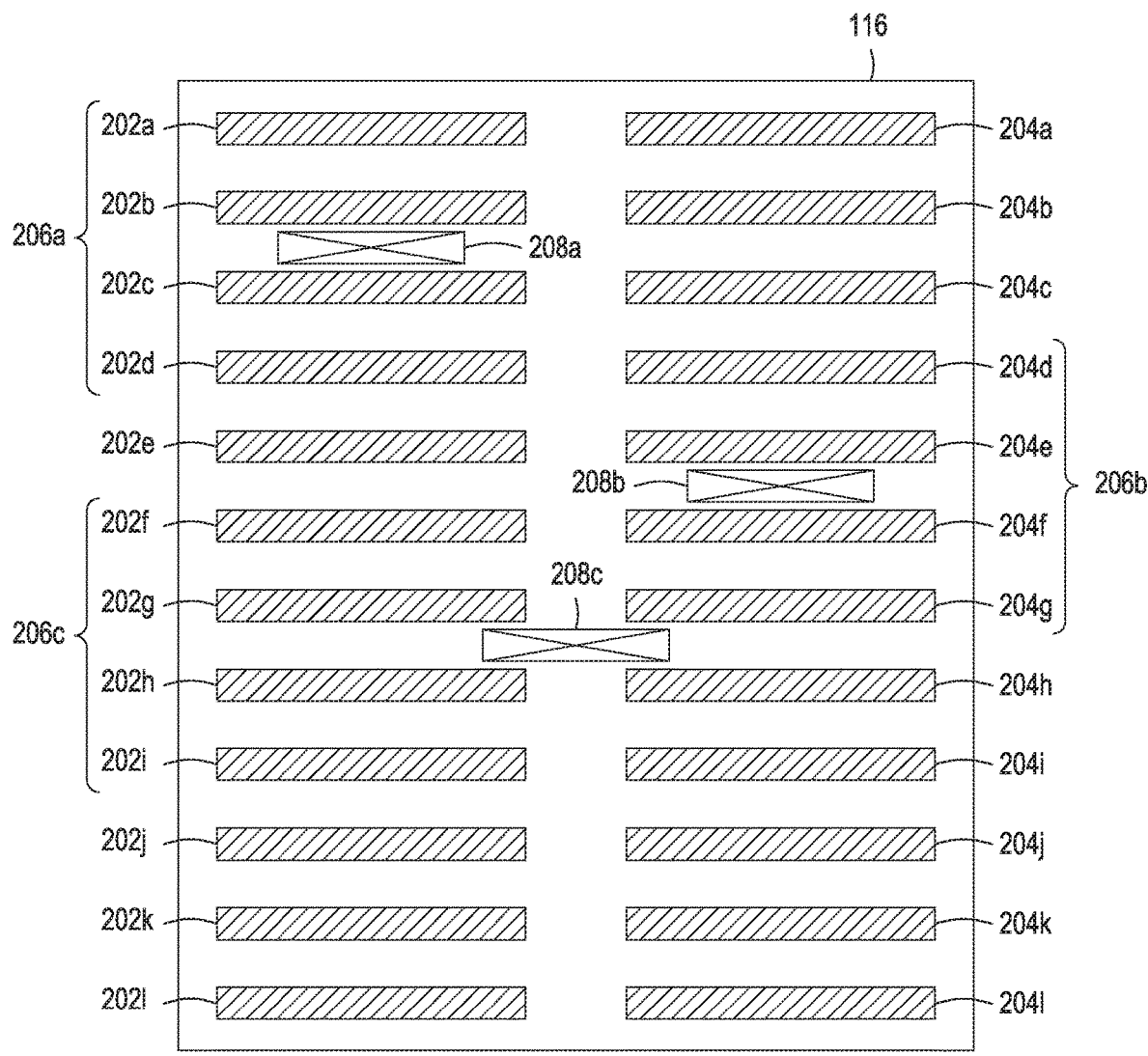
FIG. 2 is a detailed illustration of an exemplary electrode array that can be included in the tissue measuring system of FIG. 1, according to various embodiments of the present invention.

FIG. 2 is a detailed illustration of an exemplary electrode array 116 that can be included in tissue measuring system 100 of FIG. 1, according to various embodiments of the present invention. As shown, electrode array 116 includes a first column of electrodes 202a-l and a second column of electrodes 204*a-l*. Electrode array 116 includes one or more measuring subsets of electrodes 206*a-c*.

In some embodiments, the physical distance between each of the electrodes in electrode columns 202*a-l* is constant. Additionally or alternatively, the electrical paths of different electrode pairs are constant. For example, the physical distance between electrode 202*a* and electrode 202*b* could have a physical distance of 1 mm, which can be equal to a 1-mm physical distance between electrode 204*j* and 204*k*. Similarly, electrical paths formed using the respective pairs of electrodes will remain constant. For example, an electrical path that is formed when electrodes 202*a*, 202*b* to are connected electrode selector 114 is equal to an electrical path that is formed when electrodes 204*j*, 204*k* are connected to electrode selector 114.

In operation, controller 124, through electrode selector 114, selects a measuring subset 206*a*. In some embodiments, the measuring circuit includes electrodes that have the same path length. In various embodiments, selection of measuring subset 206*a* provides the advantage of avoiding synchronization issues by avoiding reflections and phase shifts when performing multiple measurements. Additionally or alternatively, the physical path length and/or the electrical path length of electrodes 202*a*-1, 204*a-l* may not be equal, but may be fixed in time. In such instances, subsequent signal processing steps may be adjusted to compensate for unequal physical path lengths and/or unequal electrical path lengths.

During a non-limiting, exemplary operation, controller 123 could measure the electrical properties of a section of an excised tissue sample located at section 208*a* by selecting measuring subset 206*a* of electrode array 116, which includes electrodes 202*a-d*. Similarly, controller 123 could measure section 208*b* by selecting measuring subset 206*b*, which includes electrodes 204*d-g*. Controller 123 could also measure section 208*c* by selecting measuring subset 206*c*, which includes electrodes 202*f-i*, 204*f-i*. In some embodiments, controller 123 may measure varying depths of the excised tissue sample by selecting a measuring subset with electrodes located further away from the section. For example, when measuring section 208*c*, controller 123 could measure a different depth of section 208*c* by selecting a measuring subset including each of electrodes 202*c-l*. When electrode selector 114 connects measuring subset 206*a* to the measuring circuit, one or more of electrodes 202*a-d* could be connected to a voltage-sensing device, one or more of electrodes 202*a-d* could be connected to a current-sensing device, while the remainder of electrodes 202*e*-1, 204*a*-1 are disconnected from the measuring circuit.

Electrode pair 202*a*, 202*d* in measuring subset 206*a* forms a current-sensing circuit. Electrode 202*a* acts as an injection electrode that receives a current from a current generator. The injection electrode 202*a* receives an alternating current that has a frequency corresponding to the operating frequency specified by controller 123. Electrode 202*d* acts as a return electrode that completes a current path by connecting to electrode 202*a*. In some embodiments, the return electrode 202*d* is connected to a current-sensing circuit or current-sensing device, such as an ammeter. Classification module 112 may receive the current measurement provided by the current-sensing circuit or current-sensing device and associate the measured current with the operating frequency of the initial current.

In some embodiments, one or more electrodes in between the electrodes forming the current-sensing circuit may be part of a voltage-sensing circuit. For example, electrodes 202*b*, 202*c* of measuring subset 206*a* could act as voltage-sensing electrodes and be connected to a voltage-sensing circuit or a voltage-sensing device, such as a voltmeter. Voltage-sensing electrodes 202*b*, 202*c* could have high impedances in order to avoid adding stray currents into the measuring circuit. Classification module 112 could receive the voltage measurement provided by the voltage-sensing circuit or voltage-sensing device and associate the measured current with the operating frequency of the initial current.

In a non-limiting exemplary embodiment, controller 123 could measure different sections of an excised tissue sample by switching to different measuring subsets 206*a*, 206*b*, 206*c*. For example, controller 123 could cause electrode selector 114 to switch from measuring section 208*a* to section 208*b* by disconnecting measuring subset 206*a* from the measuring circuit and connecting measuring subset 206*b* to the measuring circuit. In some embodiments, controller 123 may switch between sections 208*a*, 208*b*, 208*c* in a pre-defined pattern. For example, controller 123 could perform series of electrical measurements on section 208*a* for 10 to 60 seconds. Controller 123 could then cause electrode selector 114 to select a different measuring subset to perform a series of electrical measurements on a section of the excised tissue sample located between electrode 202*c* and 202*d* for 10 to 60 seconds. In some embodiments, controller 123 may perform electrical measurements all sections within electrode array 116 in under 60 to 120 seconds.

Figure 3:
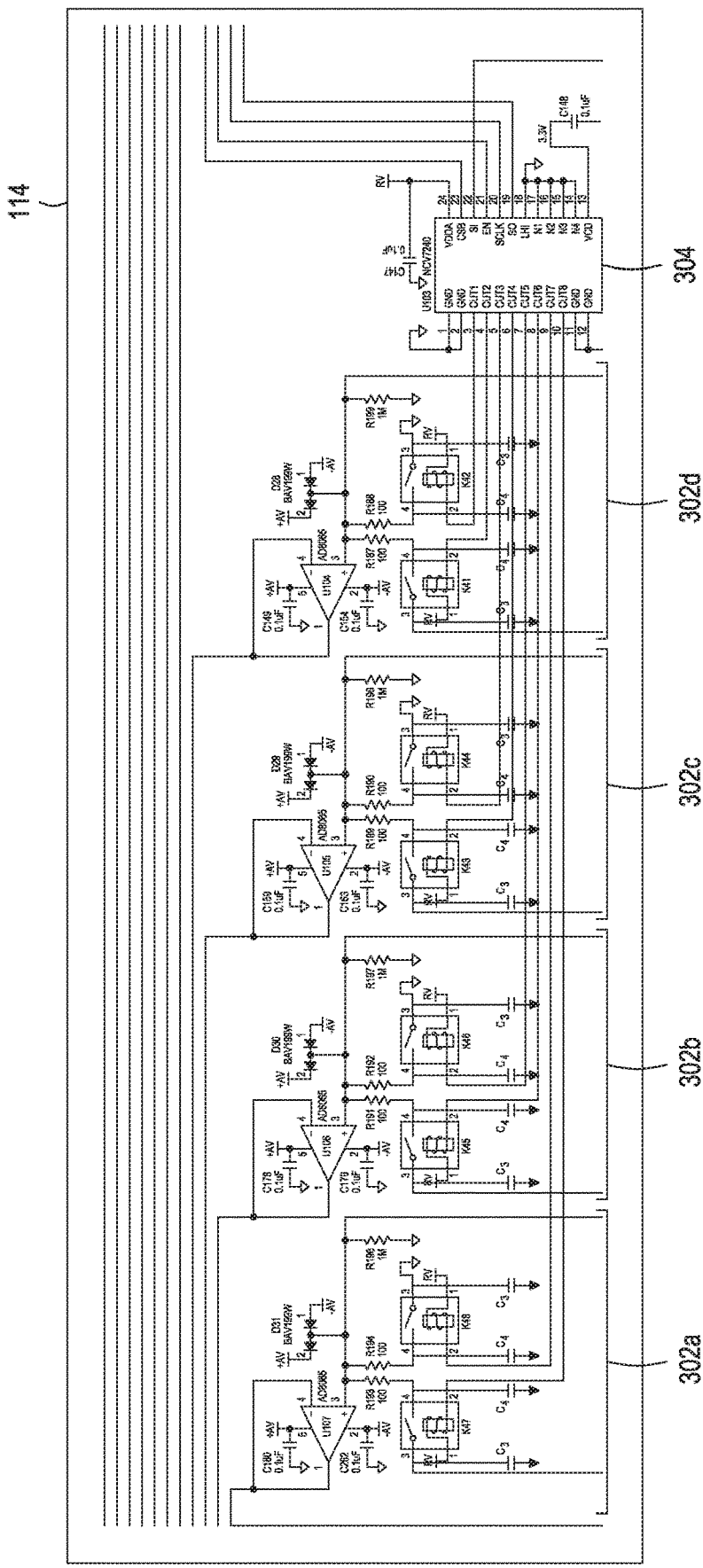
FIG. 3 is a detailed illustration of an exemplary electrode selector that can be included in the tissue measuring system of FIG. 1, according to various embodiments of the present invention.

FIG. 3 is a detailed illustration of an exemplary electrode selector 114 that can be included in tissue measuring system 100 of FIG. 1, according to various embodiments of the present invention. As shown, electrode selector 114 includes micro-relay circuits 302*a-d* connected to relay driver 304. In some embodiments, relay driver 304 may receive one or more control signals from controller 123 and connect one or more electrodes to the voltage-sensing circuit of the measuring circuit and connect one or more electrodes to the current-sensing circuit of the measuring circuit. In various embodiments, electrode selector 114 may use micro-switches that include micro-relay circuits 302*a-d* connected to relay driver 304. Additionally or alternatively, electrode selector 114 may use one or more mechanical switches to mechanically connect and/or disconnect one or more electrodes included in electrode array 116 via electrode selector 114.

When electrode selector 114 uses electronic micro-switching to connect the one or more electrodes, relay driver 304 can be a microcontroller or other electronic circuit that controls one or more micro-relay circuits 302*a-d*. In some embodiments, one or more relay drivers 304 may control each of the micro-relay circuits connected to the corresponding electrodes in electrode array 116. In some embodiments, relay driver 304 may receive control signals from controller 123 to connect electrodes to the measuring circuit. Relay driver 304 may respond to the received control signal by sending one or more driving signals to micro-relay components included in each of micro-relay circuits 302*a-d*. The driving signal may close one of the pair of micro-relay components or open each of the micro-relay components. In some embodiments, relay driver 304 switches the measuring subset 206*a* to a separate measuring subset 206*b* by sending driving signals to each of micro-relay circuits 302*a-d* corresponding to the electrodes included in measuring subsets 206*a*, 206*b*. Additionally or alternatively, when electrode selector 114 uses mechanical switching, relay driver 304 may connect electrodes to the measuring circuit using one or more mechanical switches.

Each of micro-relay circuits 302*a-d* is connected to a separate electrode in electrode array 116. In some embodiments, micro-relay circuit 302*a-d* includes an amplifier and two separate micro-relay components at the input of the amplifier. In some embodiments, relay driver 304 may open both micro-relay components, configuring the circuit to perform voltage sensing at the corresponding electrode in electrode array 116. Relay driver 304 may close the first of the two micro-relay components to connect micro-relay circuit 302a-d and the corresponding electrode to the current injection source. In some embodiments, relay driver 304 may close the second of the two micro-relay components to connect micro-relay circuit 302a-d and the corresponding electrode to the current-sensing circuit. In some embodiments, one or more of the remaining electrodes not in measuring subset 206a may be shorted to ground.

In some embodiments, a two electrode configuration may sense both the current and the voltage. In the two electrode configuration, one electrode in electrode array 116 configured for voltage sensing may simultaneously also be configured for current injection, while a second electrode configured for voltage sensing may simultaneously ale be configured for current sensing.

Micro-relay circuits 302a-d execute switching using one or more micro-relay components. The micro-relay components advantageously switch between connecting and disconnecting current injection and/or current-sensing circuits to the electrodes with a minimum of parasitic impedances or capacitances (1-2 pF) added to the measuring circuit. By avoiding the addition of such parasitic impedances and capacitances, electrode selector 114 can switch between measuring subsets 206a-c quickly without sacrificing the accuracy of the collected electrical measurements. Micro-relay circuits 302a-d also provide the advantage of using electrical switches instead of slower mechanical rotary switches.

In some embodiments, micro-relay circuits 302a-d may include one or more correction techniques to minimize crosstalk caused by one or more electrodes in electrode array 116 when a measuring subset 206a is performing an electrical measurement. For example, only the electrodes of measuring subset 206a could be connected to the measuring electronics, while all other electrodes in electrode array 116 that are not included in the measuring subset 206a could be mechanically or electrically isolated. In some embodiments, micro-relay circuits 302a-d may match impedances of the source and the sink in order to avoid reflection and phase shifts.

Figure 4:
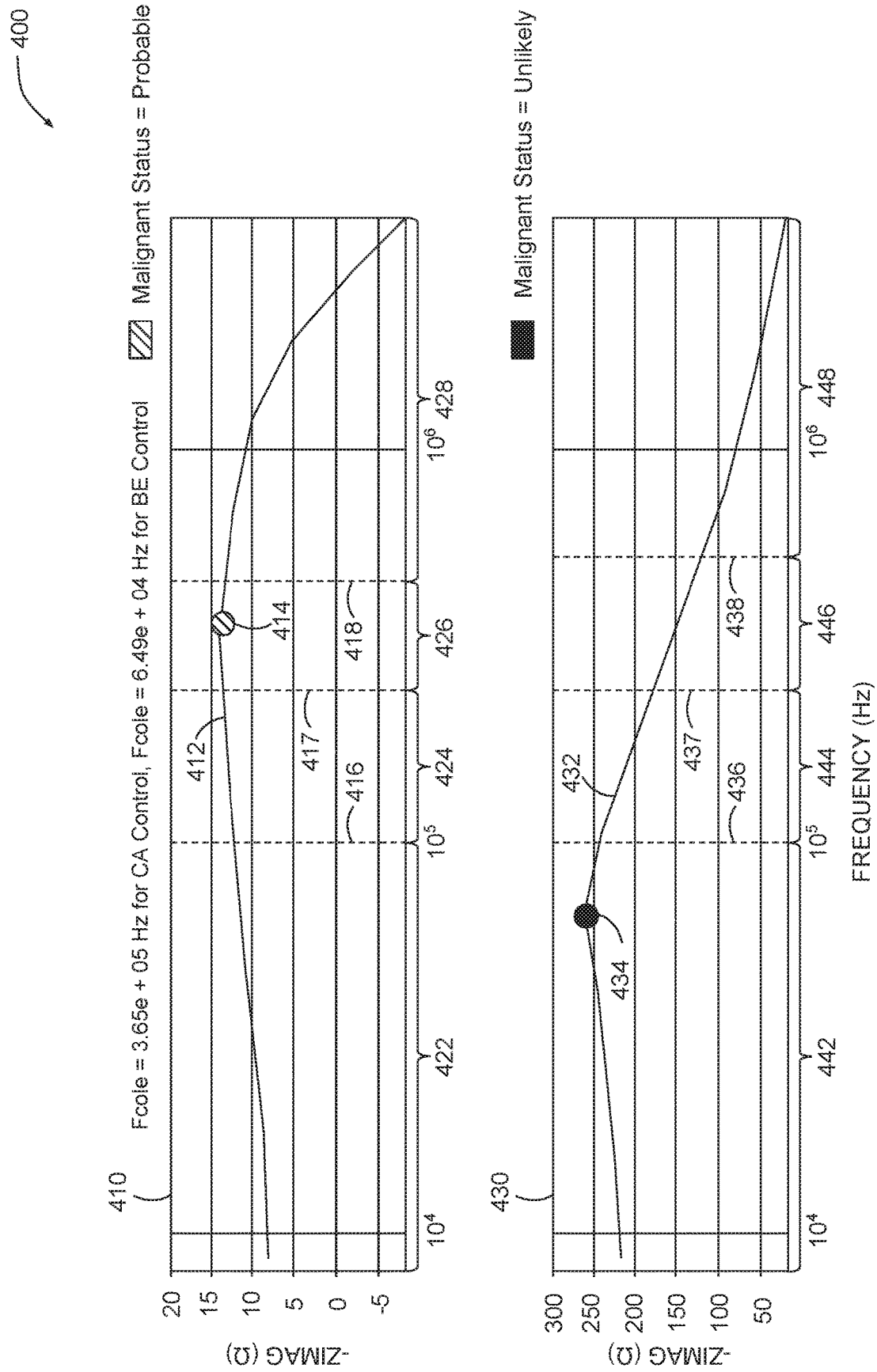
FIG. 4 illustrates computed Cole relaxation frequencies for one or more sections of excised tissue, according to various embodiments of the present invention.

FIG. 4 illustrates computed Cole relaxation frequencies for one or more sections of excised tissue, according to various embodiments of the present invention. Graphs 400 illustrate impedance spectrums indicating calculated negative reactive component of impedances for a range of operating frequencies based on voltages and currents measured by electrode array 116. Graph 410 illustrates the negative of the reactive component of impedance spectrum 412 for a section of an excised tissue sample that likely includes malignant cells. Graph 430 illustrates the negative of the reactive component of the impedance spectrum 432 for a section of an excised tissue sample that likely does not include any malignant cells.

Graph 410 includes cancer presence threshold 416, cancer recurrence threshold 417, and metastasis threshold 418. Impedance spectrum 412 includes a Cole relaxation frequency 414 corresponding to the peak of negative of the reactive component of the impedance spectrum 412. In some embodiments, analyzer 121 computes the Cole relaxation frequency 414 by generating the negative of the reactive component of the impedance spectrum 412 and determining the frequency corresponding to the peak of the curve. In other embodiments the Cole relaxation frequency is obtained as the best fit of the Cole function to both the resistive and reactive components of the impedance curve. In some embodiments, analyzer 121 may compare the Cole relaxation frequency with cancer presence threshold 416, cancer recurrence threshold 417, and/or metastasis threshold 418. In various embodiments, analyzer 121 may provide a cancer recurrence prediction based on the comparison of the Cole relaxation frequency to cancer presence threshold 416, cancer recurrence threshold 417, and/or metastasis threshold 418. Based on the comparisons, analyzer 121 determines whether the Cole relaxation frequency falls within no cancer detection range 422, cancer detection (with no recurrence) range 424, cancer recurrence and no metastasis range 426, and cancer recurrence with metastasis range 428. Similarly, analyzer 121 compares the Cole relaxation frequency to thresholds 432-438 to determine whether the Cole relaxation frequency falls within respective ranges 442-448.

In various embodiments, analyzer 121 can compare Cole relaxation frequency 414 to cancer presence threshold 416. For example, cancer presence threshold 416 could be 100 kHz. Analyzer 121 could determine that the section of the excised tissue sample likely contains malignant cells because Cole relaxation frequency 414 exceeds cancer presence threshold 416. In another example, analyzer 121 could compare the determined Cole relaxation frequency 434 for impedance spectrum 432 to cancer presence threshold 436. Analyzer 121 could determine that the section of the excised tissue sample likely does not contain malignant cells because Cole relaxation frequency 434 is less than cancer presence threshold 436, placing the Cole relaxation frequency within no cancer detection range 442. In some instances, Cole relaxation frequency 414 for a tissue sample containing malignant cancer cells is up to 1000 times larger than Cole relaxation frequency 434 for a tissue sample that does not contain any malignant cancer cells.

In some embodiments, analyzer 121 may compare Cole relaxation frequency 414 to cancer recurrence threshold 417 and/or metastasis threshold 418. For example, cancer recurrence threshold may be a value ranging from 200-400 kHz and metastasis threshold 418 may be a value ranging from 300-600 kHz. As shown, cancer recurrence threshold 417, 437 is 300 kHz and metastasis threshold 418, 438 is 600 kHz.

In operation, analyzer 121 provides the evaluation that the section of the excised tissue sample does not contain cells likely approaching a critical stage, where the critical metastasis stage indicates more-dangerous concentrations of cancer cells. Analyzer 121 provides the evaluation based on the determination that Cole relaxation frequency 414 is below metastasis threshold 418. Analyzer 121 could provide the evaluation that the section of the excised tissue sample likely does not contain cells approaching a critical stage because Cole relaxation frequency 424 is less than metastasis threshold 428. In some embodiments, analyzer 121 may compare Cole relaxation frequency 424 to multiple thresholds, where higher thresholds indicate more dangerous diagnoses, such as a higher probability of cancer, recurrence, and/or metastasis.

FIG. 5 illustrates tables showing the accuracies of cancer detection in a sample group of patients based on various computed Cole relaxation frequencies, according to various embodiments of the present invention. Tables 500 show tabulated results of diagnosis for squamous cell carcinomas (SCCs), basal cell carcinomas (BCCs), and combined results for a group of patients using tissue analysis system 100.

Table 530 shows that from a sample of 177 tests for basal cell carcinoma, tissue analysis system 100 accurately classified over 97 percent of the excised tissue samples. The accuracy of tissue analysis system 100 includes a high sensitivity rate, reflecting the rate at which tissue analysis system 100 correctly detected malignant cells in excised tissue that actually contained malignant cells. The accuracy of tissue analysis system 100 also includes a high specificity rate, reflecting the rate at which tissue analysis system 100 correctly detected no malignant cells in excised tissue that actually contained no malignant cells.

Table 520 shows that from a sample of 29 tests for squamous cell carcinoma, tissue analysis system 100 accurately classified each of the excised tissue samples. Table 510 shows that tissue analysis system 100 accurately detected the presence or absence of BCCs or SCCs in over 98 percent of excised tissue samples. Tissue analysis system 100 provides a technological improvement over prior devices in automatically detecting cancerous cells in an excised tissue sample quickly and with high accuracy.

Figure 6:
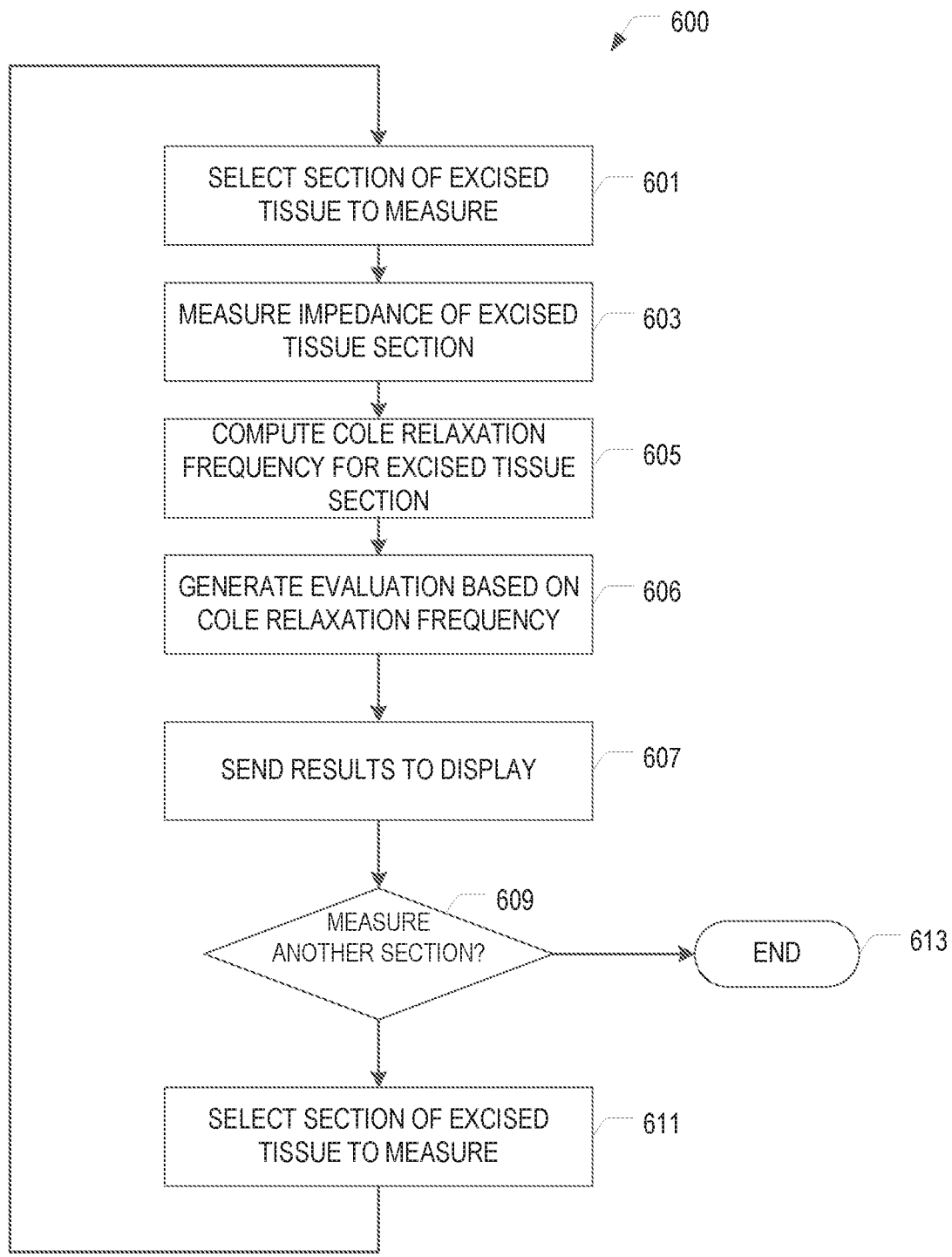
FIG. 6 is a flow diagram of method steps for automatically analyzing and assessing samples of excised tissue for cancer cells, according to various embodiments of the present invention.

FIG. 6 is a flow diagram of method steps for automatically analyzing and assessing samples of excised tissue for cancer cells, according to various embodiments of the present invention. Although the method steps described in conjunction with the systems of FIGS. 1-4, persons skilled in the art will understand that any system configured to perform the method steps, in any order, is within the scope of the invention.

As shown, a method 600 for automatically analyzing and assessing an excised tissue sample starts at step 601, where classification module 112 of tissue measurement device 110 selects a section of the excised tissue sample to measure. Controller 123 included in classification module 112 sends a control signal to electrode selector 114 to connect a measuring subset 206a of electrode array 116 that surrounds the selected section. In some embodiments, controller 123 selects the section of the excised tissue sample based on instructions from a program loaded from memory 125. In some embodiments, controller 123 selects the section of the excised tissue sample based on a user input received via I/O unit(s) 130.

At step 603, tissue measurement device 110 measures at least one impedance for a section of the excised tissue sample. In some embodiments, controller 123 may cause electrode selector 114 to sweep through operating frequencies of a measurement circuit in order to measure voltages and currents for the section of the excised tissue sample. In such instances, classification module 112 may store the measured voltage and current at each operating frequency in memory 125. Additionally or alternatively, analyzer 121 in classification module 112 may compute an impedance for a given operating frequency as a ratio of the measured voltage and the measured current.

At step 605, classification module 112 of tissue measurement device 110 computes a relaxation frequency for the section of the excised tissue sample. In various embodiments, analyzer 121 may compute the Cole relaxation frequency 414, 434 based on one or more impedances computed for the section of the excised tissue sample. In some embodiments, analyzer 121 may calculate Cole relaxation frequency 414, 434 based on the impedance at a single operating frequency. Additionally or alternatively, analyzer 121 may generate the negative of the reactive component of the impedance spectrum 412 from a set of impedances computed at multiple operating frequencies. In such instances, analyzer 121 may then compute the Cole relaxation frequency 414, 434 by determining the peak of the negative of the reactive component of the impedance spectrum impedance spectrum 412, 432 and determining the frequency at which the peak occurs.

At step 606, classification module 112 generates an evaluation based on the Cole relaxation frequency. Analyzer 121 determines the presence or absence of cancerous cells based on the Cole relaxation frequency 414, 434. In various embodiments, analyzer 121 compares the Cole relaxation frequency 414, 434 of the section of the excised tissue sample to a cancer presence threshold 416, 436. Analyzer 121 generates an indication that the section of the excised tissue sample contains cancerous cells when the Cole relaxation frequency 414, 434 exceeds the cancer presence threshold 416, 436. Additionally or alternatively, analyzer 121 compares the Cole relaxation frequency 414, 434 of the section of the excised tissue sample to a different threshold, such as cancer recurrence threshold 417, 437, and/or metastasis threshold 418, 438. Analyzer 121 generates a prediction indicating a high likelihood of cancer recurrence with metastasis when the Cole relaxation frequency 414, 434 exceeds metastasis threshold 418, 438.

At step 607, classification module 112 of tissue measurement device 110 causes one or more of the computed results and/or evaluations to be displayed. For example, classification module 112 can cause display 120 to display graphical and/or textual information displaying the computed Cole relaxation frequency 414, 434, an indication of whether cancerous cells are present in the section of the excised tissue sample, and/or a prediction of whether cancer will recur in the patient. In some embodiments, analyzer 121 may generate a mapping image that identifies the location of the cancerous cells, corresponding to the sections of the excised tissue sample that analyzer 121 determined contain cancerous cells. In such instances, analyzer 121 may send the cancer detection indicator and/or mapping image to display 120.

At step 609, classification module 112 of tissue measurement device 110 determines whether to measure another section of the excised tissue sample. In various embodiments, controller 123 may make a determination to measure another section of the excised tissue sample when executing instructions to measure multiple sections of the excised tissue sample in a pre-defined sequence. For example, controller 123 could execute instructions to measure consecutive sections of the excised tissue sample using a single column of electrodes 202a-l in electrode array 116. When controller 123 determines to measure another section, classification module 112 proceeds to step 611, otherwise, method 600 ends at step 613.

At step 613, classification module 112 of tissue measurement device 110 selects a different measuring subset 206b of electrode array 116 to measure a different section of the excised tissue sample. In some embodiments, controller 123 causes electrode selector 114 to disconnect one or more electrodes from previous measuring subset 206a and connect electrodes in measuring subset 206b to a measuring circuit. After switching to the new measuring subset 206b, tissue measurement device 110 returns to step 601.

Figure 7:
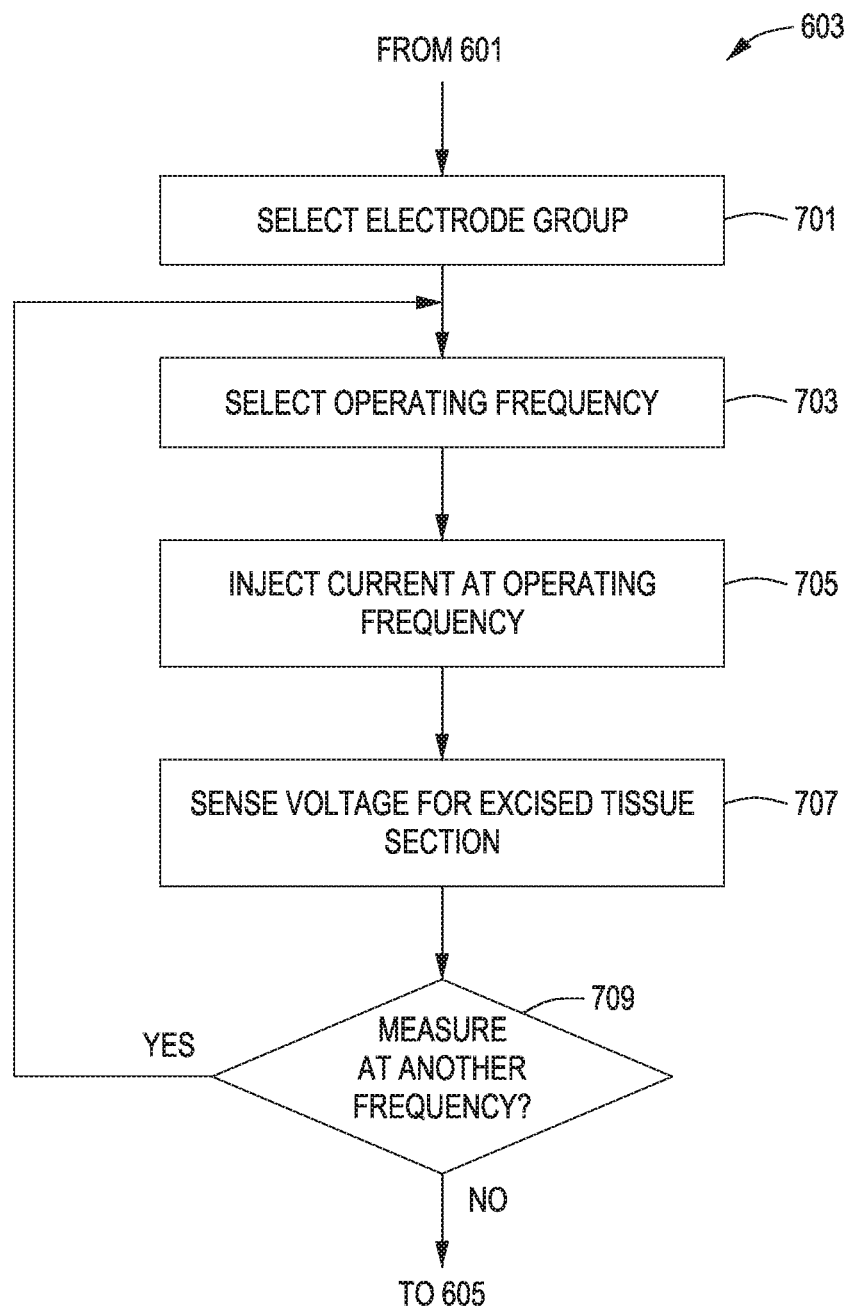
FIG. 7 is a flow diagram of method steps for detecting impedances for a section of excised tissue, according to various embodiments of the present invention.

FIG. 7 is a flow diagram of method steps for detecting impedances for a section of excised tissue, according to various embodiments of the present invention. Although the method steps described in conjunction with the systems of FIGS. 1-4, persons skilled in the art will understand that any system configured to perform the method steps, in any order, is within the scope of the invention.

Method 603 occurs between step 601 and step 605 of method 600. As shown, method 603 starts at step 701, where controller 123 of classification module 112 selects a group of electrodes to measure the select section of the excised tissue sample. Controller 123 causes electrode selector 114 to connect measuring subset 206a to measuring circuit. In some embodiments, controller 123 causes electrode selector 114 to disconnect all remaining electrodes in electrode array 116 by shorting the remaining electrodes to ground.

At step 703, controller 123 selects an operating frequency for a measuring alternating current. In some embodiments, controller 123 sends a control signal to electrode selector 114 that includes a signal generator. Controller 123 causes the signal generator in electrode selector 114 to generate a measuring signal that has an alternating current, where the frequency of the alternating current is the operating frequency.

At step 705, electrode selector 114 injects the measuring signal at the operating frequency. In some embodiments, electrode selector 114 injects the measuring signal by connecting an electrode pair in measuring subset 206 to the signal generator to close a current path. In some embodiments, the current path may include a current-sensing circuit or a current-sensing device that measures the current of the measuring signal.

At step 707, electrode selector 114 senses a voltage for the section of the excised tissue sample. In some embodiments, electrode selector 114 connects one or more electrodes 202b-c to a voltage-sensing circuit or device. The one or more electrodes 202b-c is physically located in between the electrode pair forming the current path. The one or more electrodes 202b-c provides a high-impedance voltage-sensing circuit that does not introduce stray currents into the current path carrying the measuring signal. In some embodiments, the voltage-sensing circuit measures the voltage of the section of the excised tissue sample located in between the one or more electrodes 202b-c included in the voltage-sensing circuit.

At step 709, controller 123 in classification module 112 determines whether to measure the electrical properties of the section of the excised tissue at another frequency. In some embodiments, controller 123 may change the operating frequency of the measuring signal as part of a frequency sweep to measure the same section of the excised tissue sample using multiple operating frequencies. In some embodiments, controller 123 may increase the operating frequency at a constant rate over a specified range of frequencies. For example, controller 123 could set an initial operating frequency of 1 kHz and increase the operating frequency by 50 kHz until reaching a final operating frequency of 1 MHz. When controller 123 determines that the measuring circuit is to perform measurements at another frequency, controller 123 returns to step 703, otherwise, controller 123 proceeds to step 605 of method 600.

In sum, the tissue analysis system disclosed herein enables cancerous cells to be detected automatically within a sample of excised tissue based on the measured impedances of sections of the excised tissue. A controller in the tissue analysis system uses an electrode selector to select a first subset of electrodes in an electrode array, where the first subset of electrodes transmits a current through a given section of the excised tissue. As the current is transmitted through the given section of excised tissue, an analyzer included in the tissue analysis system measures the electrical impedance of the given section of excised tissue. The analyzer then computes a Cole relaxation frequency for the given section of excised tissue based on the measured electrical impedance. The Cole relaxation frequency for the given section of excised tissue reflects the rate at which cell membranes discharge stored electrical charges. The analyzer compares the computed Cole relaxation frequency given for the section of excised tissue to one or more thresholds relating to concentration of cancerous cells in the section of excised tissue. If the computed Cole relaxation frequency for the given section of excised tissues exceeds a cancer presence threshold, then cancerous cells are considered to be present in the given section of excised tissue. Similarly, if the computed Cole relaxation frequency for the given section of excised tissues exceeds a cancer recurrence threshold, the analyzer provides a prediction that cancer will recur in a patient, but is less likely to metastasize. If the computed Cole relaxation frequency for the given section of excised tissue exceeds the threshold of cancer recurrence with metastasis, then the analyzer provides a prediction that cancer will recur with a probability of metastasis in a patient.

In some embodiments, the electrode selector includes separate micro-relays connected to each of the electrodes in the electrode array in order to prevent the electrode array from introducing crosstalk signals, stray impedances, or other parasitic electrical charges into the measured impedances of the different sections of excised tissue. In such instances, the controller causes the electrode selector to select different subsets of electrodes included in the electrode array in order to determine impedances for different sections of the excised tissue. Accordingly, the analyzer can determine the presence of cancerous cells for each section of the excised tissue based on the respective impedances measured for those sections. The analyzer also indicates each location of detected cancerous cells based on the locations of the different sections determined to include cancerous cells. In various embodiments, the electrode selector mechanically connects only the measuring subset of electrodes a single set of electronics at a given time in order to prevent crosstalk and stray impedances. In such instances, the electrode selector issues a signal that moves the single set of electrodes in order to connect the single set of electronics to the measuring subset of electrodes.

A major advantage of the disclosed techniques is that the tissue analysis system enables a user to quickly detect the presence and location of cancer cells in a tissue with a high degree of accuracy based on the computed Cole relaxation frequency. Detecting cancerous cells based on the Cole relaxation frequency enables a surgeon to maintain high accuracy when assessing excised tissue during MMS without requiring frozen section preparation and microscopic evaluation of each excised tissue layer, greatly reducing the procedural time of MMS. The reduction in time of MMS also greatly reduces the cost of performing MMS as a treatment for skin cancer.

Another advantage of the disclosed techniques is that the tissue analysis system includes micro-relay components and/or mechanical components that advantageously switch between connecting and disconnecting the electrodes to the measure the electrical properties of the excised tissue sample without introducing parasitic impedances or capacitances. Avoiding the addition of parasitic impedances and capacitances enables the tissue analysis system switch connections to different electrodes quickly without sacrificing the accuracy of the collected electrical measurements. Further, the tissue analysis system reliably analyzes excised tissue to predict the probability that cancer recurs in a patient and whether the recurrence of the cancer will eventually lead to metastasis. The disclosed system thus enables a user to reliably determine the probability of cancer recurrence, which may lead to specific treatments related to a cancer recurrence and metastasis.

1. In various embodiments, a method for predicting recurrence of cancerous cells in a patient, the method comprises measuring, by a first subset of electrodes included in an electrode array operating at a first frequency, a first impedance of a first section of a first sample of tissue excised from the patient, computing a first Cole relaxation frequency for the first section of the first sample based on the first impedance, and generating a first prediction relating to cancerous cells in the patient based at least in part on the first Cole relaxation frequency.

2. The method of clause 1, further comprising measuring, by a second subset of electrodes included in the electrode array at the first frequency, a second impedance of a second section of the first sample.

3. The method of clause 1 or 2, further comprising computing a second Cole relaxation frequency for the second section of the first sample based on the second impedance, wherein the first prediction is based on at least one of the first Cole relaxation frequency and the second Cole relaxation frequency.

4. The method of any of clauses 1-3, further comprising determining positions of cancerous cells in the first sample based on a first position associated with the first section within the first sample, and a second position associated with the second section within the first sample.

5. The method of any of clauses 1-4, further comprising measuring, by a second subset of electrodes included in the electrode array operating at the first frequency, a second impedance of the first section of the first sample, computing a second Cole relaxation frequency for the first section of the first sample based on the second impedance, and generating a second prediction relating to cancerous cells in the patient, wherein the second prediction is based on at least the first Cole relaxation frequency or the second Cole relaxation frequency.

6. The method of any of clauses 1-5, wherein the first Cole relaxation frequency comprises an average rate of electrical discharge associated with a plurality of cell membranes included in the first section of the first sample.

7. The method of any of clauses 1-6, wherein generating the first prediction comprises determining that the first Cole relaxation frequency exceeds a first threshold, and selecting, for the first prediction, a pre-defined prediction associated with exceeding the first threshold.

8. The method of any of clauses 1-7, wherein measuring the first impedance of the first section of the first sample comprises injecting, at a first electrode included in the first subset of electrodes, a first alternating current at the first frequency, returning, at a second electrode included in the first subset of electrodes, the first alternating current, and measuring, at one or more electrodes located in between the first electrode and the second electrode, a voltage associated with the first section of the first sample as the alternating current passes through the first section of the first sample.

9. In various embodiments, an apparatus for predicting recurrence of cancerous cells in a patient, the apparatus comprises a first subset of electrodes included in an electrode array that measures, while operating at a first frequency, a first impedance of a first section of a first sample of tissue excised from the patient, and an analyzer that computes a first Cole relaxation frequency for the first section of the first sample based on the first impedance, and generates a first prediction relating to cancerous cells in the patient, wherein the first prediction is based on at least the first Cole relaxation frequency.

10. The apparatus of clause 9, wherein the first subset of electrodes comprises a first electrode, a second electrode parallel to the first electrode, and a third electrode parallel to the first and second electrode, wherein a first distance between the first electrode and second electrode is equal to a second distance between the second electrode and third electrode.

11. The apparatus of clause 9 or 10, wherein the first subset of the electrodes comprises a first electrode that injects a first alternating current at the first frequency, a second electrode that returns the first alternating current, and at least one third electrode located in between the first electrode and the second electrode, wherein the at least one third electrode is measures a voltage associated with the first section of the first sample as the alternating current passes through the first section of the first sample.

12. The apparatus of any of clauses 9-11, further comprising a selector connected to the electrode array, wherein the selector is electrically connects the first subset of electrodes and electrically disconnect all remaining electrodes included in the electrode array when the first subset of electrodes measures the first impedance.

13. The apparatus of any of clauses 9-12, further comprising a second subset of electrodes included in the electrode array that measures, at the first frequency, a second impedance of a second section of the first sample, and a controller that electrically connects, via the selector, the first subset of electrodes when measuring the first impedance, and electrically connects, via the selector, the second subset of electrodes when measuring the second impedance.

14. The apparatus of any of clauses 9-13, wherein the apparatus generates the first prediction by determining that the first Cole relaxation frequency exceeds a first threshold, and selecting, for the first prediction, a pre-defined prediction associated with exceeding the first threshold.

15. The apparatus of any of clauses 9-14, wherein the first frequency is a frequency between 1 kHz and 25 MHz.

16. The apparatus of any of clauses 9-15, wherein at least one electrode included in the electrode array comprises a platinum electrode.

17. The apparatus of any of clauses 9-16, wherein each electrode included in the electrode array comprises a non-invasive electrode that is substantially flat when contacting the first sample.

18. In various embodiments, one or more non-transitory computer-readable media include instructions that, when executed by one or more processors, cause the one or more processors to perform the steps of measuring, by a first subset of electrodes included in an electrode array operating at a first frequency, a first impedance of a first section of a first sample of tissue excised from a patient, computing a first Cole relaxation frequency for the first section of the first sample based on the first impedance, and generating a first prediction relating to cancerous cells in the patient based at least in part on the first Cole relaxation frequency.

19. The one or more non-transitory computer-readable media of clause 18, wherein the instructions further cause the one or more processors to perform the steps of measuring, by a second subset of electrodes included in an electrode array at the first frequency, a second impedance of the first section of the first sample, computing a second Cole relaxation frequency for the first section of the first sample based on the second impedance, and generating a second prediction relating to cancerous cells in the patient, wherein the second prediction is based on at least the first Cole relaxation frequency or the second Cole relaxation frequency.

20. The one or more non-transitory computer-readable media of clause 18 or 19, wherein generating the first prediction comprises determining that the first Cole relaxation frequency exceeds a first threshold, and selecting, for the first prediction, a pre-defined prediction associated with exceeding the first threshold.

Any and all combinations of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A method for generating a prognosis of recurrence of cancerous cells in a patient, the method comprising:
    measuring, by a first subset of electrodes included in an electrode array operating at a first frequency, a first impedance of a first section of a first sample of tissue excised from the patient;
    computing a first Cole relaxation frequency for the first section of the first sample based on the first impedance;
    determining that the first Cole relaxation frequency exceeds a first threshold;
    in response to determining that the first Cole relaxation frequency exceeds the first threshold, determining that cancerous cells are present in the first sample;
    determining that the first Cole relaxation frequency exceeds a second threshold; and
    in response to determining that the first Cole relaxation frequency exceeds the second threshold, generating a first prognosis of recurrence of cancerous cells in the patient.

2. The method of claim 1, further comprising measuring, by a second subset of electrodes included in the electrode array operating at the first frequency, a second impedance of a second section of the first sample.

3. The method of claim 2, further comprising computing a second Cole relaxation frequency for the second section of the first sample based on the second impedance, wherein the first prognosis is based on at least one of the first Cole relaxation frequency or the second Cole relaxation frequency.

4. The method of claim 3, further comprising determining positions of cancerous cells in the first sample based on a first position associated with the first section within the first sample, and a second position associated with the second section within the first sample.

5. The method of claim 1, further comprising:
    measuring, by a second subset of electrodes included in the electrode array operating at the first frequency, a second impedance of the first section of the first sample;
    computing a second Cole relaxation frequency for the first section of the first sample based on the second impedance; and generating a second prognosis relating to cancerous cells in the patient, wherein the second prognosis is based on at least the first Cole relaxation frequency or the second Cole relaxation frequency.

6. The method of claim 1, wherein the first Cole relaxation frequency comprises an average rate of electrical discharge associated with a plurality of cell membranes included in the first section of the first sample.

7. The method of claim 1, wherein generating the first prognosis comprises selecting, for the first prognosis, a pre-defined prognosis associated with the first Cole relaxation frequency exceeding the second threshold.

8. The method of claim 1, wherein measuring the first impedance of the first section of the first sample comprises:
   injecting, at a first electrode included in the first subset of electrodes, a first alternating current at the first frequency;
   returning, at a second electrode included in the first subset of electrodes, the first alternating current; and
   measuring, at one or more electrodes located in between the first electrode and the second electrode, a voltage associated with the first section of the first sample as the alternating current passes through the first section of the first sample.

9. An apparatus for generating a prognosis of recurrence of cancerous cells in a patient, the apparatus comprising:
   a first subset of electrodes included in an electrode array that measures, while operating at a first frequency, a first impedance of a first section of a first sample of tissue excised from the patient; and
   an analyzer that:
      computes a first Cole relaxation frequency for the first section of the first sample based on the first impedance;
      determines that the first Cole relaxation frequency exceeds a first threshold;
      in response to determining that the first Cole relaxation frequency exceeds the first threshold, determines that cancerous cells are present in the first sample;
      determines that the first Cole relaxation frequency exceeds a second threshold; and
      in response to determining that the first Cole relaxation frequency exceeds the second threshold, generates a first prognosis of recurrence of cancerous cells in the patient.

10. The apparatus of claim 9, wherein the first subset of electrodes comprises:
   a first electrode;
   a second electrode parallel to the first electrode; and
   a third electrode parallel to the first and second electrodes,
   wherein a first distance between the first electrode and second electrode is equal to a second distance between the second electrode and third electrode.

11. The apparatus of claim 9, wherein the first subset of the electrodes comprises:
   a first electrode that injects a first alternating current at the first frequency;
   a second electrode that returns the first alternating current; and
   a third electrode located in between the first electrode and the second electrode,
   wherein the third electrode measures a voltage associated with the first section of the first sample as the alternating current passes through the first section of the first sample.

12. The apparatus of claim 9, further comprising a selector connected to the electrode array, wherein the selector electrically connects the first subset of electrodes and electrically disconnects all remaining electrodes included in the electrode array when the first subset of electrodes measures the first impedance.

13. The apparatus of claim 12, further comprising:
   a second subset of electrodes included in the electrode array that measures, at the first frequency, a second impedance of a second section of the first sample; and
   a controller that:
      electrically connects, via the selector, the first subset of electrodes when measuring the first impedance, and
      electrically connects, via the selector, the second subset of electrodes when measuring the second impedance.

14. The apparatus of claim 9, wherein the analyzer generates the first prognosis by selecting, for the first prognosis, a pre-defined prognosis associated with the first Cole relaxation frequency exceeding the second threshold.

15. The apparatus of claim 9, wherein the first frequency is a frequency between 1 kHz and 25 MHz.

16. The apparatus of claim 9, wherein at least one electrode included in the electrode array comprises a platinum electrode.

17. The apparatus of claim 9, wherein each electrode included in the electrode array comprises a non-invasive electrode that is substantially flat when contacting the first sample.

18. One or more non-transitory computer-readable media including instructions that, when executed by one or more processors, cause the one or more processors to perform steps of:
   measuring, by a first subset of electrodes included in an electrode array operating at a first frequency, a first impedance of a first section of a first sample of tissue excised from a patient;
   computing a first Cole relaxation frequency for the first section of the first sample based on the first impedance;
   determining that the first Cole relaxation frequency exceeds a first threshold;
   in response to determining that the first Cole relaxation frequency exceeds the first threshold, determining that cancerous cells are present in the first sample;
   determining that the first Cole relaxation frequency exceeds a second threshold; and
   in response to determining that the first Cole relaxation frequency exceeds the second threshold, generating a first prognosis of recurrence of cancerous cells in the patient.

19. The one or more non-transitory computer-readable media of claim 18, wherein the instructions further cause the one or more processors to perform steps of:
   measuring, by a second subset of electrodes included in the electrode array operating at the first frequency, a second impedance of the first section of the first sample;
   computing a second Cole relaxation frequency for the first section of the first sample based on the second impedance; and
   generating a second prognosis relating to cancerous cells in the patient, wherein the second prognosis is based on at least the first Cole relaxation frequency or the second Cole relaxation frequency.

20. The one or more non-transitory computer-readable media of claim 18, wherein generating the first prognosis comprises:

selecting, for the first prognosis, a pre-defined prognosis associated with the first Cole relaxation frequency exceeding the second threshold.

\* \* \* \* \*